United States Patent [19]

McFarlane

[11] Patent Number: 4,909,632
[45] Date of Patent: Mar. 20, 1990

[54] METHOD FOR SELECTING PERSONAL COMPATIBLE COLORS

[76] Inventor: Darby McFarlane, St. Adde 10 E. End Ave., New York, N.Y. 10021

[21] Appl. No.: 355,041

[22] Filed: May 15, 1989

Related U.S. Application Data

[63] Continuation of Ser. No. 239,041, Aug. 29, 1988, abandoned, which is a continuation of Ser. No. 65,620, Jun. 30, 1987, abandoned, which is a continuation of Ser. No. 833,661, Feb. 21, 1986, abandoned, which is a continuation of Ser. No. 514,618, Jul. 18, 1983, abandoned.

[51] Int. Cl.$^4$ .............................................. G01J 3/46
[52] U.S. Cl. ................................... 356/402; 356/421; 434/99
[58] Field of Search ................ 356/300, 326, 402–421, 356/425; 364/498, 526; 434/98–100

[56] References Cited

U.S. PATENT DOCUMENTS

| | | |
|---|---|---|
| 205,578 | 7/1878 | Rose et al. |
| 1,629,330 | 5/1927 | Adler |
| 1,741,080 | 12/1929 | Stenz |
| 1,979,119 | 10/1934 | Radzinsky |
| 2,221,774 | 11/1940 | Bowser |
| 3,533,399 | 10/1970 | Goldberg et al. |
| 4,135,497 | 12/1979 | Meyers et al. |
| 4,241,738 | 12/1980 | Lübbers et al. ...................... 356/40 |
| 4,302,971 | 12/1981 | Luk |
| 4,357,106 | 11/1982 | Tschirren |

FOREIGN PATENT DOCUMENTS 1236984 3/1967 Fed. Rep. of Germany .
1468339 12/1966 France .

OTHER PUBLICATIONS

Jackson, *Color Me Beautiful*, New York, Ballantine Books, Apr. 1981, pp. 25, 26, color palettes, 37–39, 41–59, 61–74, 143–147.

Pinckney et al., *Your New Image Through Color & Line*, Calif., Fashion Image/Crown Summit Books, Sep. 1981, pp. 1–3, 17, 21–29, 97–105, 111, 112, 120–127.

*Primary Examiner*—F. L. Evans
*Attorney, Agent, or Firm*—Brumbaugh, Graves, Donohue & Raymond

[57] ABSTRACT

A method for the selection of proper colors for individual wearers depending upon the underlying color of the skin of the wearer and the intensity thereof. The method includes the steps of providing a group of classifications of color temperature, preferably four in number, and using a spectrophotometer, or a draping technique of material to determine the color temperatures of the skin of the user, and a determination of the classification in which those color temperatures fall is made. A predetermined group of colors are classified within each category, so that upon determination of the proper classification for an individual user, reference may be made to the proper predetermined group of colors as a guide for appropriate apparel, cosmetic make up, or hair tint selection.

8 Claims, 1 Drawing Sheet

METHOD FOR SELECTING PERSONAL COMPATIBLE COLORS

This application is a continuation of application Ser. No. 239,041, filed on 8/29/88, now abandoned, which is a continuation of Appln. S/N 065,620, filed 6/30/87, now abandoned, which is a continuation of Appln. S/N 833,661 filed on 2/21/86, now abandoned, which is a continuation of Appln. S/N 514,618 filed 7/18/83 now abandoned.

BACKGROUND OF THE INVENTION

This invention relates generally to the field of individual grooming, and more particularly to an improved method for selecting proper colors of individual articles of apparel, cosmetic make up or hair tint, the method being suitable for use by persons having only ordinary skills.

It has long been appreciated that garments, cosmetic make up or hair tint, of particular colors are more flattering to a wearer than similar items of other colors. Many persons, particularly women, possess the ability almost instinctively to make a selection, without appreciating the basis which enables them to make a subjective consideration and decision. Some persons are aware that the proper selection is directly related to the complexion of the wearer, but have not appreciated the actual relationship which exists. As a result, it is customary to try garments, cosmetic make up or hair tint on a trial basis, and observing the appearance in a mirror, or consulting with a salesperson.

BRIEF SUMMARY OF THE INVENTION

I have found that the process of color selection can be materially simplified by the provision of standard categories, relatively few in number, of skin colors into which both Caucasian and American black persons may be classified, depending upon the underlying or subcutaneous skin color. Practically all such normal persons have an underlying tone of either blue or yellow-red in varying degrees of intensity, which results in the presence of a readily determined color temperature which may be measured by a draping technique done visually or by a color temperature measuring device or spectrophotometer. The output of a color temperature measuring device is a measure of the yellow to blue content of the light it receives. Where such temperature is to be measured to relatively large tolerances, it may be accomplished by using hand held color temperature meters. The result with a spectrophotometer will be a plottable curve covering the visual spectrum, which will show strength of varying degrees over the spectrum. This curve is matched with curves which are obtained by similar measurements of colors on fabrics or paper samples, which will exhibit similar blue and yellow red reflective properties. Practically all of the colors in the spectrum are available in each of the categories, for selection, provided that the particular color exhibits a curve which is similar to that obtained by measuring the skin pigmentation of the individual user.

DETAILED DESCRIPTION OF THE DISCLOSED METHOD

In accordance with the invention, a first step consists in the establishment of a number of skin color categories. Each of the colors in each category exhibits a substantially similar plotted curve extending over the visible spectrum, obtained by spectroanalysis.

I have found that a compilation of four sets of basic color ranges in material fabric can be made that is most compatible with the four ranges of basic skin pigment undertones into which the great bulk of the population may be classified. These skin and fabric color categories are as follows:

Classification A includes almost all of the colors of the visible spectrum. They have the highest intensity (50 to 100%) per spectrum analysis of the shorter wave lengths of the skin color spectrum, that is to say, the "blue base" tones. Black is also in this classification.

Classification B also includes most all colors, with the exclusion of black. They have the next highest or one to fifty percent intensity per spectrum analysis of the shorter wave lengths of the skin color spectrum, or the "blue based" tones.

Classification C also includes most of the colors, and these have a one to fifty percent intensity of the yellow-red tones, or the longer wave lengths of the skin color spectrum, per spectrum analysis.

Classification D, again, includes most of the colors, and they have the highest intensity of the yellow-red tones, fifty to one hundred percent, or the longest wave lengths of the skin color spectrum, per spectrum analysis.

Figure 1:
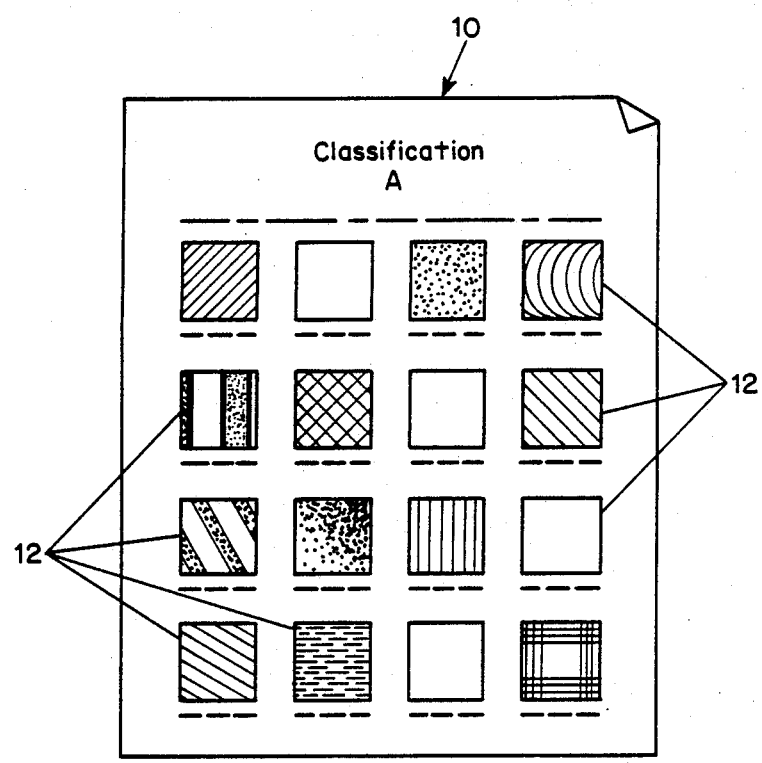
FIG. 1 is a diagrammatic illustration of a color chart collecting together colors compatible with one category of skin color.

As both the skin color undertones of an individual person and the labeling of the color of a dyed piece of material can be classified into one of the above four categories, it is possible to match the skin of the user to the material and determine the most compatible colors in a given material a person may wear, or use on their person. Once the classification of the individual user is established, it is possible to provide that person with a simplified color chart 10, as shown for example in FIG. 1, and the selection of a garment or articles to be worn may be matched as closely as possible from the standpoint of color to a color 12 on the chart.

Figure 2:
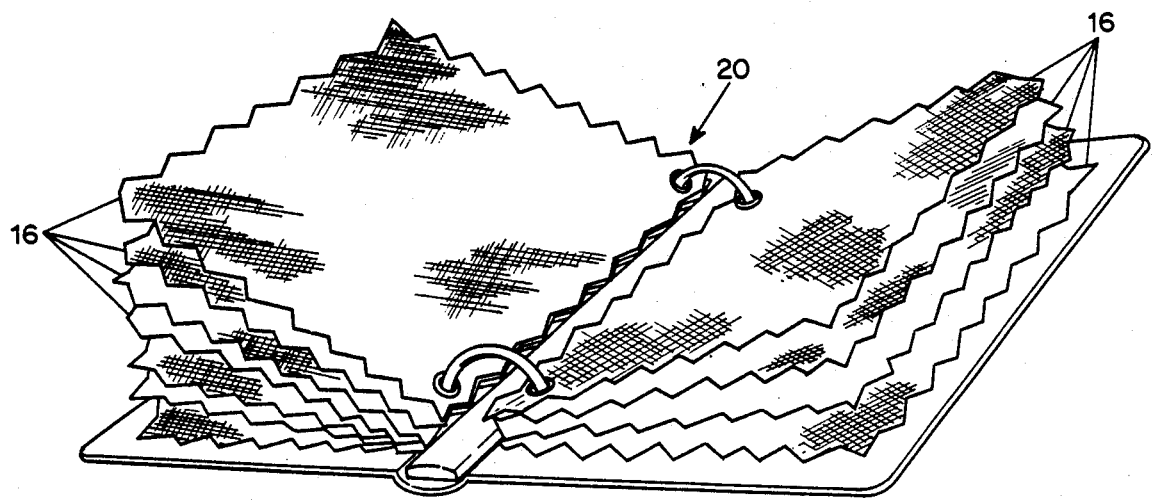
FIG. 2 is a perspective view of an assemblage of fabric samples having colors compatible with one category of skin color.

As a next step in the disclosed method, a series of color charts 10 are prepared in which suitable colors 12 for each category are assembled. This might be done by displaying the colors on a single surface, or preferably individual swatches of fabric 16 exhibiting the proper colors can be assembled in a convenient package 20, as shown for example in FIG. 2.

Individual testing of a subject is conducted using a draping technique of material around the shoulders, near the face, the materials being of the full color spectrum, but being either blue-based or red-yellow based and observed visually as to compatibility to the skin pigment of the subject, or by use of a spectrometer, or by means of a specialized color temperature meter calibrated to indicate broadly in which of the four categories A through D the skin of the subject is properly classified. Once this reading has been made, the subject is supplied with the appropriate color chart, and selection of a garment, cosmetic make up or hair tint can be guided by comparing the apparent color thereof with colors 12 on the chart 10. While in most cases, the user will want to try the garment, make up or hair tint, as a practical matter, the chart is useful in facilitating an initial rejection of an item based upon improper color alone.

It will be understood by those skilled in the art that it is possible to provide a greater number of categories with correspondingly greater precision relative to the availability of colors. I have found, however, for practical purposes, the four category system is entirely adequate, and greater precision can be used in such case, with regard to the selection of colors to be included in the color chart relating to a particular category, thus facilitating the testing of an individual user which may be conducted by those who are relatively unskilled in the physical sciences.

I wish it to be understood that I do not consider the invention limited to the precise details of structure shown and set forth in this specification, for obvious modifications will occur to those skilled in the art to which the invention pertains.

I claim:

1. A method of determining color compatibility of an individual person with non-skin matter such as apparel and cosmetics; the method including establishing color compatibility categories exclusively on the basis of skin color content in the bluer and yellower regions of the spectrum, determining the compatibility of non-skin matters with the skin colors in the categories, measuring by instrument the content in an individual person's skin coloration of color content from said bluer and yellower regions of the spectrum, and assigning the individual to a preestablished category exclusively on the basis of the skin color content thus measured.

2. The method of assigning to non-skin matter a skin color compatibility classification comprising:
   (a) providing a plurality of color classification categories based exclusively upon measurable skin color content in bluer and yellower regions of the spectrum,
   (b) identifying compatibility of at least one color of the non-skin matter with one of the classification categories, and
   (c) assigning one of a plurality of color classifications to the non-skin matter based on the identified compatibility.

3. The method according to claim 2, including providing a plurality of colors assigned to the same color classification in a color chart.

4. The method according to claim 2, including collecting together in an assemblage a plurality of samples of non-skin matter having the same color classification.

5. The chart made by the method according to claim 3.

6. The assemblage made by the method according to claim 4.

7. The method of making a color chart of the colors of non-skin matter for compatibility with skin colors including:
   (a) determining a classification for colors of non-skin material for compatibility with skin color classification categories based exclusively upon measurable skin color content in bluer and yellower spectral regions, and
   (b) assembling representations of the colors similarly classified to form a chart of colors of at least that classification as an indication of appropriate color selections for individuals having a skin color classification category.

8. A color chart including:
   (a) representations of colors of non-skin products such as garments, cosmetics, hair tint or the like, and
   (b) said representations of colors being assembled together and being of colors of a single classification compatible with a skin color classification category based exclusively upon measurable skin color content in bluer and yellower spectral regions.

* * * * *